Figure 1:
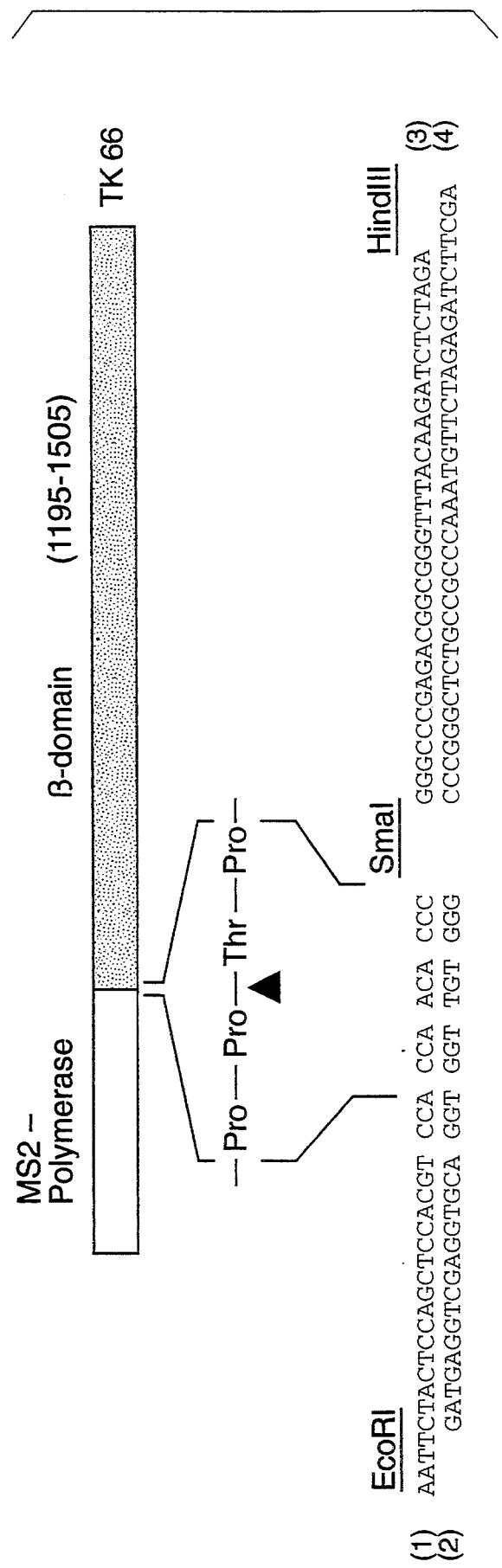

United States Patent [19]

Meyer et al.

[11] Patent Number: 5,427,927
[45] Date of Patent: Jun. 27, 1995

[54] PROCESS FOR THE ENZYMATIC CLEAVAGE OF RECOMBINANT PROTEINS USING IGA PROTEASES

[75] Inventors: Thomas F. Meyer; Johannes Pohlner, both of Tübingen; Günter Schumacher, Bernried; Carola Dony, Starnberg, all of Germany

[73] Assignee: Max-Planck-Gesellschaft Zur Förderung Der Wissenschaften E.V., Gottingen, Germany

[21] Appl. No.: 917,034

[22] PCT Filed: Feb. 1, 1991

[86] PCT No.: PCT/EP91/00192

§ 371 Date: Aug. 30, 1992

§ 102(e) Date: Aug. 30, 1992

[87] PCT Pub. No.: WO91/11520

PCT Pub. Date: Aug. 8, 1991

[30] Foreign Application Priority Data

Feb. 3, 1990 [DE] Germany ............... 40 03 149.7
May 17, 1990 [DE] Germany ............... 40 15 921.3
May 17, 1990 [DE] Germany ............... 40 15 922.1
Dec. 10, 1990 [DE] Germany ............... 40 39 415.8

[51] Int. Cl.$^6$ ............... C12P 21/02; C12N 15/24; C07K 14/535
[52] U.S. Cl. ............... 435/69.7; 435/69.52; 435/252.3; 435/252.33; 435/320.1; 530/351; 536/23.4
[58] Field of Search ............... 435/69.5, 69.52, 69.7, 435/320.1, 252.3, 252.33; 424/12; 530/351; 536/23.4, 23.5

[56] References Cited

U.S. PATENT DOCUMENTS

| | | | |
|---|---|---|---|
| 4,543,329 | 9/1985 | Daum et al. | 435/69 |
| 4,828,988 | 5/1989 | Bollen et al. | 435/68 |
| 5,047,333 | 10/1991 | Grandi et al. | 435/68.1 |
| 5,055,555 | 10/1991 | Sassenfeld | 530/351 |
| 5,073,627 | 12/1991 | Curtis et al. | 530/351 |
| 5,087,564 | 2/1992 | Mai et al. | 435/69.7 |
| 5,100,784 | 3/1992 | Latta et al. | 435/69.7 |

FOREIGN PATENT DOCUMENTS

| | | |
|---|---|---|
| 0215126 | 3/1987 | European Pat. Off. . |
| 0220520 | 5/1987 | European Pat. Off. . |
| 0256843 | 2/1988 | European Pat. Off. . |
| 0344796 | 12/1989 | European Pat. Off. . |
| 9006370 | 6/1990 | WIPO . |

OTHER PUBLICATIONS

Mulks, M. H., et. al. (1982) J. Infect Dis. 146(2), 266–274.
Kilian, M., et. al, (1983) Am. N.Y. Acad. Sci. 469, 612–624.
Jambou, R. C., et. al. (1988) Proc. Natl. Acad. Sci., USA 85, 9426–9430.
Hopp, T. P., et. al. (1988) Biol Tech, 6, 1204–1210.
Pohlner, J., et. al, (1987) Nature 325, 458–462.
Pricker, et, al, (1983) Proc. Natl. Acad. Sci, USA 80, 2681–2685.
Souza, L. M., et. al. (1986) Science 232, 61–65.
Wood, S. G., et. al, (1991) Infec. Immun. 59(5), 1818–1822.

*Primary Examiner*—Charles L. Patterson, Jr.
*Attorney, Agent, or Firm*—Felfe & Lynch

[57] ABSTRACT

For the enzymatic cleavage of fusion proteins and for the isolation of desired components of these fusion proteins (1) a junction region, in which two components of the fusion protein are joined together, is modified by means of genetic engineering so that at least one IgA protease recognition site with the amino acid sequence Y-Pro-!-X-Pro is formed in this junction region, in which X can be any amino acid and Y can be one or several arbitrary amino acids, (2) the fusion protein which results from step (1) is cleaved by IgA protease at the position in the recognition site marked with -!- and (3) after the cleavage one or several desired components of the fusion protein are isolated.

57 Claims, 4 Drawing Sheets

PROCESS FOR THE ENZYMATIC CLEAVAGE OF RECOMBINANT PROTEINS USING IGA PROTEASES

The invention concerns a process for the sequence-specific cleavage of proteins obtained biotechnologically using IgA proteases (also denoted Igases) and in particular a process for the production of recombinant proteins or peptides in prokaryotes and the subsequent removal of a N-terminal sequence.

The biotechnological preparation of proteins is preferably carried out using microorganisms which can be easily cultured and which allow the isolation of the protein which is produced in a simple manner. Suitable microorganisms for this are e.g. the gram-negative bacterium Escherichia coli, the gram-positive bacterium Streptococcus carnosus as well as the baker's yeast Saccharomyces cerevisiae. The expression of authentic foreign genes in such microorganisms is, however, often disadvantageous. In E. coli, for example, the amino-terminal methionine residue of natural proteins which is a result of translation is usually efficiently cleaved off by proteases. In the case of foreign proteins the first methionine residue is, however, usually only partially cleaved off. A suitable procedure for the production of such proteins with a defined amino end is therefore first to produce these in the form of fusion proteins and subsequently to cleave them in a defined way with a sequence-specific protease.

Compared to authentic proteins, such fusion proteins can in addition have the advantage that they aggregate in the cell of the microorganism and form dense precipitation bodies ("inclusion bodies") which can easily be separated from other cellular components and thus facilitate the isolation and purification of the desired protein. On the other hand, carrier proteins which are initially fused to the actual desired protein by means of genetic engineering procedures impart a particular stability against unspecific proteolytic degradation to the fusion partner; the problem of degradation of polypeptides which are recognized as being foreign concerns in particular the biotechnological preparation of small peptides. Furthermore, other carrier proteins allow the desired proteins to be directed into particular cell compartments from which they can be particularly easily purified and where they are particularly stable and/or where they are accessible for test purposes. Finally, carrier proteins can also have special properties which allow an efficient purification e.g. by affinity chromatography. For most application purposes fusion proteins are preferred which carry the carrier protein at the amino end and the desired protein at the carboxyl end. However, the opposite version or the coupling of the desired protein with two fusion partners can also be desirable in particular cases. In addition, the reiteration of the desired protein within one fusion can be advantageous.

In order to obtain the desired protein in a free form from such a fusion, it is necessary to cleave the covalently bound fusion partners from one another. In principle this can be achieved by chemical or biochemical (enzymatic) methods. However, the limited specificity of the methods which have been hitherto available is a limitation in this process, for in order to obtain the desired protein it is important that such a cleavage takes place in a cleavage sequence between the fusion partners, i.e. the junction region, but under no circumstances additionally within the desired protein itself. The cleavage of the fusion partners must therefore be carried out highly specifically.

Chemical processes which have been used up to now for the sequence-specific separation of fusion proteins are for example the cleavage by cyanogen bromide at the amino acid methionine within a protein and the cleavage between the amino acids Asp.!.Pro in an acid medium using formic acid. These processes are only then suitable when the specific cleavage site in the desired protein does not occur again apart from in the region of the junction to the fusion partner. However, in general, biochemical cleavage procedures are preferable to chemical methods because the former can usually be carried out under physiological or at least mild chemical reaction conditions which do not damage the desired protein.

Biochemical methods for the cleavage of fusion proteins are based on the use of proteases which are as specific as possible. For example, trypsin cleaves peptide bonds within proteins which follow the amino acids arginine and lysine. The specificity can be increased by a prior chemical modification of the amino acid Lys, by means of which the specific recognition can be limited to the amino acid arginine. A further protease which is used biotechnologically is clostripain; this enzyme cleaves peptide bonds between the amino acids arginine and any amino acid which follows it. A review of the enzymatic procedures for the cleavage of fusion proteins which have been used up to now has been drawn up by F. A. O. Marston (In [D. M. Glover, E.]: DNA cloning III, IRL Press Oxford and Washington DC, 1987). Enzymatic cleavage procedures are also limited in that the amino acid(s) which are specific for the cleavage site can at the same time also occur in the desired protein itself. Therefore for the biochemical cleavage of protein fusions, enzymes are particularly suitable which, in order to cleave, not only recognize one amino acid but rather a sequence of amino acids since the probability that a particular amino acid sequence is present once again in the desired protein in addition to the cleavage site between the fusion partners is less the larger the number of amino acids necessary for the recognition and cleavage of a cleavage sequence.

Proteases which cut a particular protein very specifically are known. The majority of such selective proteases (which occur e.g. in the complement system and blood coagulation system of humans) cleave at a defined site in the substrate, but, when the corresponding cleavage region is transferred into another protein (e.g. a fusion protein) such proteases are as a rule no longer able to cleave. The reasons for this are numerous and are because for example the protease recognizes a particular secondary or tertiary structure in the substrate or because of the inaccessibility of the cleavage site in fusion proteins.

The list of sequence-specific proteases which up to now have been used to a limited extent for the cleavage of fusion proteins is at present headed by factor Xa. This protease specifically cuts the cleavage sequence Ile-Glu-Gly-Arg.!.X, in which .!. represents the cleavage site and X denotes an arbitrary amino acid. It has however turned out that this protease also cannot generally be used for the cleavage of fusion proteins which have a corresponding cleavage sequence in their junction region; such substrates (i.e. fusion proteins which contain a desired protein covalently bound to a carrier protein) are often not cleaved at all or only to a limited extent or only in a soluble form.

An efficient cleavage of fusion proteins is particularly important in the production of recombinant proteins in prokaryotic organisms. In this case it is necessary to clone a DNA sequence which contains an ATG as an initiation codon before the start of the actual DNA sequence. As a consequence thereof a recombinant protein is expressed in prokaryotes such as e.g. E. coli which contains a methionine residue at amino acid position −1.

In many cases it is, however, necessary to prepare recombinant proteins which are free of methionine in position 1. The isolation of such proteins from prokaryotes can e.g. be carried out via a methionine-specific peptidase which cleaves off the N-terminal methionine. This process is, however, very cumbersome since the cleavage can only be checked by means of protein sequencing. In addition, the separation of protein containing methionine in position −1 and methionine-free protein is very difficult because of their almost identical molecular weight and can thus only be achieved to a partial extent.

The PCT application WO84/02351 discloses the cleavage of N-terminal amino acids from a fusion protein. In this process several amino acids of the protein can be removed from the N-terminus up to a sequence X-Pro by stepwise cleavage by an exopeptidase, preferably leucine peptidase. The sequence X-Pro is cleaved from this product either in two steps or in a one-step reaction using postproline-dipeptidyl-aminopeptidase (EC 3.4.14.). This process has, however, the disadvantage that as a result of the stepwise cleavage of amino acids from the N-terminus of the protein a uniform product cannot be formed but instead a mixture of products must always be formed which contains incompletely degraded proteins as well as proteins which have been degraded too much in addition to the desired product.

A further process for the enzymatic cleavage of a fusion protein is known from the European Patent No. 0 020 290. In this process the enzyme collagenase is used to cleave the fusion component of a protein from a particular recognition sequence. Afterwards further amino acids of the fusion component can be subsequently removed by further enzymatic treatment. It was, however, established that collagenase and also other endopeptidases have only a low specificity (see Biochim. Biophys. Acta 271 (1972), 133–144). Moreover, the collagenases are only active on proteins which have a specific spatial structure.

The use of the already-mentioned factor Xa for cleaving off a N-terminal fusion component of proteins is already known. However, apart from the already-mentioned problems of cleavage efficiency this process has further disadvantages in that internal sequences of the protein may also be recognized and cleaved. In addition, factor Xa has to be isolated from bovine serum and as a consequence when it is used to cleave proteins for therapeutic applications an extensive purification and analysis is necessary afterwards in order to detect pathogenic factors or viruses which may be present.

Various pathogenic bacterial species (e.g. of the genus Neisseria, such as Neisseria gonorrhoea and Neisseria meningitis or the genus Haemophilus such as Haemophilus influenzae and Haemophilus aegypticus) which grow on human mucous membranes secrete proteases whose sequences are closely interrelated and are specific for human IgA1 and are therefore comprehensively denoted IgA proteases or Igases. The immunoglobulin IgA1 is an important component of the secretory immune response which should protect against infections by such pathogenic organisms (review: Kornfeld and Plaut, Rev. Infect. Dis. 3 (1981), 521–534). In addition, the IgA protease also cleaves its own precursor protein by autoproteolysis. The formation of the IgA protease from Neisseria gonorrhoeae MS11 in the authentic bacterial strain as well as in gram-negative host cells has already been described in detail (DE 36 22 221.6).

IgA protease cleaves the following recognition sequences as described e.g. by Pohlner et al., (Nature 325 (1987), 458–462):

1. Pro-Ala-Pro-!-Ser-Pro
2. Pro-Pro-!-Ser-Pro
3. Pro-Pro-!-Ala-Pro
4. Pro-Pro-!-Thr-Pro

Here the symbol .!. denotes in each case the cleavage site of the IgA protease. The cloning of the IgA protease is e.g. described by Pohlner et al., 1987, supra.

It is therefore the object of the present invention to provide an improved process for the biochemical (enzymatic) cleavage of fusion proteins in order that fusion proteins produced by genetic engineering consisting of any fusion partners and a specific cleavage sequence in the junction region can be used as a substrate for the isolation of the desired protein in as high a yield as possible and reproducibly.

This object was achieved using genetic engineering by the introduction of the recognition site or cleavage sequence Pro-!-X-Pro in the junction region of fusion proteins and by the specific cleavage of this cleavage sequence by an IgA protease at the cleavage site marked with .!. in which X preferably represents the amino acids Ser, Thr and Ala and particularly preferably Ser or Thr but can also represent other amino acids.

The present invention therefore provides a process for the enzymatic cleavage of fusion proteins and for the isolation of desired components of these fusion proteins which is characterized in that (1) a junction region, in which two components of the fusion protein are joined together, is modified by means of genetic engineering so that at least one IgA protease recognition site with the amino acid sequence Y-Pro-!-X-Pro is formed in this junction region, in which X can be any amino acid and Y can be one or several arbitrary amino acids, (2) the fusion protein which results from step (1) is cleaved by IgA protease at the position in the recognition site marked with .!. and (3) after the cleavage one or several desired components of the fusion protein are isolated.

In accordance with the present invention the term "IgA protease" includes proteases which specifically cleave IgA and which are described for example in Rev. Infekt. Dis.3 (1981) 521–534. Recombinant IgA proteases such as those described in DE-A 36 22 221, Proc. Natl. Acad. Sci. USA 79 (1982) 7881–7885, Proc. Natl. Acad. Sci. USA 80 (1983) 2681–2685, Nature 325 (1987) 458–462 and EMBO Jour. 3 (1984) 1595–1601 are also just as suitable.

In the process according to the present invention the modification of a junction region of fusion proteins is preferably carried out in such a way that nucleotide sequences are incorporated in the junction region of a fusion protein which code for an IgA protease recognition site or a part thereof whereby these nucleotide sequences are incorporated upstream or/and downstream of one or more DNA sections encoding desired parts of the protein fusion. Nucleotide sequences which have been synthesized chemically are preferably used for this purpose.

Surprisingly, it was established that the process according to the present invention is also especially suitable for the cleavage of fusion proteins which did not originally (i.e. before the modification of the junction region) have a natural IgA protease recognition site.

The IgA protease recognition site for the process according to the present invention has the amino acid consensus sequence Y-Pro.!.X-Pro. In this case X denotes any amino acid and Y denotes one or several arbitrary amino acids. X preferably denotes serine, threonine or alanine and particularly preferably serine or threonine. Y preferably represents several amino acids which end with the sequence Pro, Pro-Ala, Arg-Pro, Pro-Arg-Pro, Ala-Pro-Arg-Pro or Pro-Ala-Pro-Arg-Pro.

The process according to the present invention therefore comprises the incorporation of an IgA protease recognition site with at least the consensus cleavage sequence Pro.!.X-Pro, which can be used to cleave off and isolate the desired protein by IgA protease, into the junction region of any fusion protein, e.g. between a carrier protein and the desired protein. For this the amino acids Ser, Ala or Thr are preferably used in the cleavage sequence Pro.!.X-Pro at position X. In order to further optimize the cleavage at the marked site further special amino acids can precede the cleavage sequence, in particular the amino acid Pro.

Particularly preferred are the amino acid sequences:
a) Pro-Ala-Pro.!.Ser-Pro,
b) Pro-Pro-!.Ser-Pro,
c) Pro-Arg-Pro-Pro.!.Ala-Pro
d) Pro-Pro.!-Thr-Pro,
e) Ala-Pro-Arg-Pro-Pro.!.Thr-Pro or
f) Pro-Ala-Pro-Arg-Pro-Pro.!.Thr-Pro.

When the process according to the present invention is applied to the cleavage of fusion proteins in which the desired protein is downstream of a carrier protein, a protein is formed after cleavage by IgA protease whose amino terminus is characterized by the sequence X-Pro. This sequence, as part of the desired protein, can be advantageous, disadvantageous or of no consequence. This sequence is in general advantageous when the desired protein obtained by genetic engineering also contains the corresponding two amino acids X-Pro in its natural form at its amino terminus. Proteins which are characterized by an amino-terminal X-Pro which are of biotechnological importance occur naturally.

The process according to the present invention has the advantage over all other known processes for the cleavage of fusion proteins that surprisingly it can be universally applied to fusion proteins which have the above-mentioned cleavage sequence in their junction region and that it can be applied to insoluble, soluble, membrane-associated and cell-bound protein fusions as well. In addition, a particular advantage is that the process enables fusion proteins or protein fusions to be cleaved in the form of precipitation bodies such as those which form in microorganisms and where they can be easily concentrated as such. A further advantage of the process is that the cleavage enzyme used, Igase can be easily isolated from the culture media of non-pathogenic bacteria.

The incorporation of the cleavage sequence for Igase into the junction region of a protein fusion is carried out by means of genetic engineering. Thus, for example, a series of nucleotides or a nucleotide sequence which code for a cleavage sequence or a part thereof can be chemically synthesized and incorporated between the DNA sections for a carrier protein and a desired protein by means of known genetic engineering methods. A natural sequence of nucleotides which codes for a suitable cleavage sequence or a part thereof can also be incorporated in a corresponding manner. The gene coding for a protein fusion is preferably placed under the control of suitable (preferably inducible) expression signals so that fusion proteins can be produced according to the requirements. Suitable prokaryotic or eukaryotic (plant as well as animal) cells can be used as host cells for the production of protein fusions; cell-free systems are, however, also possible. The carrier proteins used in these processes can have any function depending on which properties they should impart to a protein fusion such as particular transport functions, functions which improve the purification of the protein fusion or its stability, and many others. Preferred carrier proteins are elucidated below.

The cleavage of protein fusions in accordance with the present invention is preferably carried out with Igase which is formed by an overproducing non-pathogenic bacterial strain and is isolated by purification from culture supernatants (see e.g. DE-36 22 221).

The process according to the present invention can be used for preparative as well as for analytical purposes. In the preparative application the process serves the biotechnological production of important proteins which can be used e.g. in medicine, in research, in environmental protection or in industrial processes or products. In an analytical application the process can, for example in combination with suitable expression systems, be used for the routine examination of gene fusions.

A preferred embodiment of the process according to the present invention for the enzymatic cleavage of fusion proteins and isolation of desired components of these fusion proteins is characterized in that (1) a cell is transformed with a recombinant DNA or a recombinant vector, in which the DNA or the vector contains at least one copy of a gene which codes for a fusion protein which contains at least one IgA protease recognition site in a junction region, (2) the transformed cell is cultured in a suitable medium, (3) the gene coding for the fusion protein is made to express in the transformed cell, (4) the fusion protein is cleaved with IgA protease and (5) one or several desired components of the fusion protein are isolated.

In this process the treatment of the fusion protein with IgA protease can take place in the medium (culture broth), after cell lysis or/and after partial or complete separation of cellular proteins.

In order to treat a fusion protein, preferably a prokaryotic expression product, it is in addition preferred that the IgA protease is immobilized in a manner known to the expert, for example as described in EP-B 0 141 223 or EP-B 0 141 224.

A particularly preferred application of the process according to the present invention is the production of recombinant proteins or peptides without a N-terminal methionine residue from fusion proteins or peptides having the amino acid sequence Met-Y-Pro.!-X-Pro-A, in which X represents any amino acid and preferably Thr, Ala or Set, Y represents one or several arbitrary amino acids which preferably end with Pro if X represents Thr or Ala, or preferably end with the sequence Pro-Ala or with Pro-Pro if X represents Set, and A represents any amino acid sequence. In this process the fusion protein or peptide is cleaved with IgA protease and a cleavage product having the amino acid sequence X-Pro-A is obtained. For example this process for the production of recombinant proteins from prokaryotic cells without a N-terminal methionine residue comprises the following steps:

(1) a prokaryotic cell is transformed with a gene which codes for a protein or peptide with the amino acid sequence Met-Y-Pro.!.X-Pro-A, in which X, Y and A have the above-mentioned meanings, (2) the transformed cell is cultured in a suitable medium and the transformed gene is expressed, (3) the expression product from the transformed cell having the amino acid sequence Met-Y-Pro.!.X-Pro-A is cleaved by IgA protease and (4) the resulting cleavage product which has the amino acid sequence X-Pro-A without a N-terminal methionine residue is isolated.

By means of the process according to the present invention it is possible in one step to obtain proteins in a surprisingly high yield and with good specificity which do not have a N-terminal methionine residue and which have the N-terminal sequence X-Pro, in which X preferably denotes Thr, Ala or Ser.

The carrier component Y of the fusion protein denotes an amino acid sequence with at least 1, preferably up to 100, particularly preferably 1 to 50 amino acids, which ends with a cleavage sequence which is recognized by the IgA protease. If X represents the amino acid serine then Y preferably ends with the sequence Pro-Ala or Pro. If X represents Thr or Ala then Y preferably ends with Pro and particularly preferably with Arg-Pro, Pro-Arg-Pro or Ala-Pro-Arg-Pro.

In a particularly preferred embodiment Y represents at least 5 amino acids which end with the sequence Pro-Ala -Pro-Arg-Pro. However, all cleavage sites which are recognized by IgA protease are suitable for the process according to the present invention.

The carrier component Y can in addition contain further arbitrary amino acids, preferably up to 100 and particularly preferably up to 50 amino acids. However, those amino acid sequences are preferably used for this which at the DNA level increase expression of the protein Met-Y-Pro.!.X-Pro-A or/and, at the the amino acid level, facilitate its purification from the cell.

The expression of the protein Met-Y-Pro.!.X-Pro-A can for example be improved at the DNA level by fusion with fragments of the β-galactosidase gene i.e. the carrier component Y contains a part of the β-galactosidase protein. Other alternatives for increasing the expression of the protein Met-Y-Pro.!.X-Pro-A are known to the expert. The purification and separation of the expression product can be facilitated by fusion with other polypeptides in particular with polypeptides or proteins that are highly charged (e.g. poly(Lys, Arg)) or which can bind to particular substances with high affinity (e.g. streptavidin) (see e.g. EP-A 0 089 626, EP-A 0 306 610).

In addition, the present invention provides a fusion protein which contains several polypeptide components and which has one or several IgA protease recognition sites with the amino acid sequence Pro.!.X-Pro incorporated in at least one junction region between different polypeptide components in which X denotes any amino acid but preferably Ser, Thr or Ala. The recognition site has particularly preferably the amino acid sequence (a) Pro-Ala-Pro.!.Ser-Pro, (b) Pro-Pro.!. Ser-Pro, (c) Pro-Arg-Pro-Pro.!.Ala-Pro, (d) Pro-Pro.!. Thr-Pro, (e) Ala-Pro-Arg-Pro-Pro.!.Thr-Pro or (f) Pro-Ala-Pro-Arg-Pro-Pro.!.Thr-Pro, in which .!. represents the cleavage site.

The present invention also especially encompasses a protein or peptide having the amino acid sequence Met-Y-Pro.!. X-Pro-A, in which X preferably represents Thr, Ala or Ser, Y denotes one or several arbitrary amino acids, and preferably ends with Pro if X represents Thr or Ala or ends with the sequence Pro-Ala or Pro if X represents Set, and A denotes any arbitrary amino acid sequence. Such a protein or peptide is expressed according to the present invention by transformation of a prokaryotic cell with a recombinant vector which contains at least one copy of a gene which codes for such a protein or peptide.

The sequence A can represent any amino acid sequence. Within this amino acid sequence there is preferably no further cleavage site for the IgA protease.

The present invention also provides a recombinant DNA which codes for a protein or peptide according to the present invention and in which one or several IgA protease recognition sites or cleavage sequences are incorporated in at least one junction region of the fusion protein.

A recombinant DNA according to the present invention can be obtained in a manner known to one skilled in the area of molecular biology. For this a vector which contains a DNA sequence coding for the amino acid sequence A is usually cleaved with restriction endonuclease(s) in the region of the 5' end of this gene and religated with oligonucleotides which contain the desired sequence. In this process the oligonucleotide must contain a sequence which codes for a cleavage site of the IgA protease or a part thereof.

In addition, the invention also provides a recombinant vector which contains at least one copy of a recombinant DNA according to the present invention. Vectors which are suitable as a basis for protein expression in prokaryotic organisms are known to the expert. This vector is preferably one which allows a high expression of the recombinant DNA according to the present invention. The recombinant DNA on the vector is preferably under the control of an inducible expression signal (e.g. λ, tac, lac or trp promoter).

The vector according to the present invention can be present extrachromosomally (e.g. plasmid) as well as integrated in the genome of the host organism (e.g. bacteriophage lambda). The vector according to the present invention is preferably a plasmid. Vectors which are suitable in each case for gene expression in a particular host organism are known to one skilled in the area of molecular biology. It can be a eukaryotic vector, but preferably a prokaryotic vector. Examples of suitable vectors for the expression of the DNA according to the present invention in prokaryotes are for instance commercially available pUC and pUR vectors.

The invention also provides a cell, preferably a prokaryotic cell, particularly preferably an E. coli cell which is transformed with the recombinant DNA according to the present invention or/and with a recombinant vector according to the present invention.

Examples of proteins which have the N-terminal sequence X-Pro, in which X denotes Thr, Ala or Ser and which can be obtained in one step by the process according to the present invention are for instance human erythropoietin, the β-chain of the human T-cell receptor and especially the human granulocyte stimulating factor (G-CSF).

G-CSF is synthesized as lymphokine by activated monocytes, macrophages as well as by a series of other cell lines. Lymphokines participate in the maturation of cells of the immune or blood cell system. They stimulate the maturation of bone marrow stem cells to well-differentiated cells. Thus, G-CSF induces e.g. the formation of neutrophils and granulocytes.

Since G-CSF is able to considerably increase the population of neutrophil cells within a short period this results in considerable therapeutic fields of application for G-CSF. Thus, G-CSF could e.g. be used after chemotherapy in cancer in which the cells of the immune system are destroyed. In addition, one could use G-CSF in bone marrow transplantations, in severe burn wounds, in opportunistic infections caused by immune deficiency and in leukaemia.

G-CSF is a secretory protein molecule. The primary translation product therefore contains a N-terminal signal sequence which is cleaved off when it is secreted so that the sequence of mature G-CSF begins with the amino acids Thr(+1)-Pro(+2)(amino acid positions +1 and +2). When G-CSF is produced in prokaryotes this signal peptide is either cleaved off poorly or not at all so that in order to prepare G-CSF from prokaryotes without a signal sequence an AUG(Met) must be cloned as the initiation codon before the start of the DNA sequence coding for mature G-CSF which begins with Thr(+1)-Pro(+2) at the protein level. As a consequence thereof a G-CSF is expressed in prokaryotes such as E. coli that contains a methionine at amino acid position −1.

By means of the process according to the present invention a G-CSF which is free of methionine in amino acid position −1 and which begins with the amino acids Thr(+1)-Pro(+2) can be produced in a simple manner from prokaryotes.

This is carried out by isolating a G-CSF derivative from prokaryotes which contains the amino acids Thr(+1)-Pro(+2) in position +1 and +2 of the amino acid sequence and before that, from position −1 of the amino acid sequence onwards, an amino acid sequence which can be recognized by IgA protease and which can be cleaved from the amino acid sequence G-CSF which begins with Thr(+1)-Pro(+2).

In a preferred embodiment, the derivative contains a Pro in each position −1 and −2, the amino acid sequence Arg -Pro-Pro in position −3 to position −1, the amino acid sequence Pro-Arg-Pro-Pro in position −4 to −1 or the amino acid sequence Ala-Pro-Arg-Pro-Pro in position −5 to position −1.

In a particular preferred embodiment the derivative contains the amino acid sequence $$
\begin{array}{cccccc}
-6 & -5 & -4 & -3 & -2 & -1 \\
\text{Pro} & \text{Ala} & \text{Pro} & \text{Arg} & \text{Pro} & \text{Pro}
\end{array}
$$

from position −6 to position −1. Within the meaning of the invention G-CSF is understood to include naturally occurring G-CSF, the sequence of which is for example disclosed in Science 232 (1986) 61, as well as derivatives derived therefrom with granulocyte-stimulating activity whose amino acid sequences begin with X(+1)-Pro(+2). X represents Thr, Set or Ala and particularly preferably Thr.

The G-CSF derivative according to the present invention can be cleaved by treatment with IgA protease between position +1 and −1 (between Thr(+1) and Pro(−1)) after expression in prokaryotes. Thus, a G-CSF which is free of methionine in position −1 is obtained in a single hydrolysis step and whose amino acid sequence begins N-terminally with the amino acids Thr(+1)-Pro(+2) of the naturally occurring G-CSF.

When G-CSF is expressed in prokaryotes, sparingly soluble aggregates (refractile bodies) are formed which are inactive. Before the protein can be used e.g. for therapeutic purposes it must be transformed into its active form. Using procedures which are familiar to those skilled in the art (cf. e.g. EP-A 0 219 874, EP A 0 114 506, WO 84/03711) first a solubilization is carried out by addition of denaturing agents which is followed by renaturation and, if desired, further purification steps. The treatment of the protein according to the present invention with IgA protease can take place before the solubilization, after solubilization or not until after the renaturation. If the treatment with IgA protease is to be carried out directly after solubilization, the solubilizing agent (e.g. guanidine hydrochloride or urea) must be removed by dialysis before addition of the IgA protease. However, the treatment with IgA protease is preferably carried out after renaturation since in this case the yields of G-CSF are particularly high.

The conditions required for the treatment of G-CSF or another protein to be cleaved with IgA proteases are not critical. In this process it is, however, preferred that the ratio by weight of G-CSF (or another protein) to IgA protease is 1:1 to 100:1. The reaction preferably takes place in a buffered aqueous solution of pH 6.5 to 8.5. The buffer concentration is preferably in the range between 50 and 300 mmol/l if desired, with addition of 20–100 mmol/l sodium chloride. The cleavage is preferably carried out at room temperature for 20–60 minutes.

After solubilization, renaturation and cleavage with IgA protease the cleavage product obtained in this way is preferably purified by means of ion exchange and fractionation by size. The G-CSF produced in this way which is free of methionine in position −1 is contaminated by other proteins by less than 0.1%, preferably less than $10^{-3}\%$.

G-CSF free of methionine in position −1 can therefore be almost quantitatively separated or purified from the fusion protein containing methionine by cleavage with IgA protease.

By means of the process according to the present invention a recombinant G-CSF can be obtained from prokaryotes which is contaminated by other proteins by less than 0.1%, preferably less than $10^{-3}\%$ and is quantitatively free of a G-CSF from prokaryotes which contains a methionine in position −1.

The invention also provides a pharmaceutical preparation based on a G-CSF from prokaryotes as the active substance obtained by the process according to the present invention, if desired, together with conventional pharmaceutical carriers, filling materials and auxiliary agents. Such a pharmaceutical preparation is particularly suitable for therapeutic treatments in which the formation of granulocytes, in particular of neutrophils, should be stimulated.

The pharmaceutical preparations according to the present invention can be preferably applied as injection solutions and infusion solutions. This can be done by providing a solution which is already injectable and which contains the composition according to the present invention. It is, however, also possible to provide the pharmaceutical preparations in the form of lyophilisates. These are then reconstituted with known agents or solutions which are suitable for injection purposes. Water is preferably used as the injection medium which contains the usual additives for injection solutions such as stabilising agents, solubilizers, buffers and isotonic additives such as a physiological NaCl concentration. Such additives are for example mannitol, tartrate or citrate buffer, ethanol, complexing agents such as e.g. ethylenediamine tetraacetic acid and non-toxic salts thereof, as well as high molecular polymers such as liquid polyethylene oxide for the regulation of the viscosity. Liquid carriers for injection solutions must be sterile and are preferably dispensed in ampoules.

Finally, the present invention also encompasses the use of G-CSF from prokaryotes which is free of methionine in position −1 for the production of pharmaceutical preparations according to the present invention.

In the event that a protein X-Pro-A is obtained as the product resulting from the cleavage of any fusion protein by the process according to the present invention (in which X denotes any amino acid and A denotes any arbitrary sequence of amino acids) which protein, however, carries at its amino terminus an undesired dipeptide X-Pro, then this undesired dipeptide can be separated off as a part of the process according to the present invention by further treatment with dipeptidyl aminopeptidase (DPAP). Dipeptidyl aminopeptidases have been found up to now in a series of microorganisms, insects, amphibians and in different human tissues. They aid for example in the stepwise processing of precursor proteins and some have a substantial specificity for the amino terminal degradation of the dipeptide X-Pro (X-Pro-DPAPase; G. Kreil, Trends in Biochemical Sciences 15, 23–26, 1990). Thus, desired proteins can be produced with any amino-terminal amino acids by the combination according to the present invention of Igase and X-Pro-DPAP.

It is then possible with the combination of Igase and X-Pro-DPAP described above to also produce proteins with another N-terminal amino acid sequence from prokaryotes which are free of methionine in position −1. For this a fusion protein is first obtained which has the amino acid sequence Met-Y-Pro.!.X-Pro-A, in which in this case the amino acid sequence A without the two N-terminal amino acids X-Pro is the desired component of the protein to be expressed.

The expression product of the prokaryotic cell having the amino acid sequence Met-Y-Pro.!.X-Pro-A is first cleaved with IgA protease so that a first cleavage product having the amino acid sequence X-Pro-A is formed.

This protein can then be treated with a dipeptidyl aminopeptidase as described above which specifically recognizes the sequence X-Pro and cleaves behind Pro. In this way a second cleavage product is formed having the arbitrary amino acid sequence A. The process according to the present invention has thus proven to be extremely useful for the production of very different proteins without a N-terminal methionine residue and is not limited to the production of proteins having the N-terminal sequence X-Pro in which X preferably represents Ser, Thr or Ala.

Finally the invention also encompasses a recombinant DNA which contains a region coding for an IgA protease recognition site (as defined above) and which is suitable for incorporation into a junction site of fusion proteins. This is preferably a chemically synthesized DNA fragment on the ends of which are preferably one or several suitable restriction cleavage sites.

Definition of terms:

The process according to the present invention encompasses the biotechnological production of desired proteins. In this connection biotechnological is understood as the production of a desired protein or an intermediary product of the same by use of genetic engineering methods and other biotechnological procedures (e.g. fermentation of microorganims).

A desired protein is an intermediate product or a final product which can for example be used in the field of medicine, in research, in environmental protection or in industrial processes or products.

The process according to the present invention comprises the formation of a desired protein from a fusion protein (also denoted protein fusion) in which the fusion protein or the protein fusion is composed of several fusion partners which are covalently bound to one another. In this connection at least one of the fusion partners represents a desired protein. The order of the fusion partners and their degree of repetition in a fusion protein is arbitrary; it, however, preferably consists of an amino-terminal carrier protein and a carboxy-terminal desired protein.

A carrier protein or a carrier component serves to provide the desired protein in the form of a fusion protein with certain properties. Such properties can for example result in an increased stability of the fusion proteins which is based on particular structural features and thus also in an increased resistance to cellular proteases or they can even lead to the transport of the fusion proteins to an environment with less proteolytic activity. In addition, the carrier protein can encompass properties which allow an efficient purification of tile fusion proteins. These include e.g. the binding of particular ligands in connection with affinity chromatography methods, the deposition of the fusion proteins in precipitation bodies which can be easily isolated and the transport of the proteins to easily accessible sites.

The regions within a fusion protein in which the components (carrier proteins and desired proteins) of a fusion protein are joined to one another are denoted junction regions.

Each junction region can be defined by one or several amino acid sequences. The amino acid sequences (and also all other sequences of amino acids and proteins) are understood and shown from the amino terminus (left) in the direction of the carboxy terminus (right).

Within the scope of the process according to the present invention all those amino acid sequences in the junction regions which should be cleavable by IgA proteases contain the cleavage sequence or recognition sequence according to the present invention.

That site between two amino acids of an amino acid sequence at which the cleavage of fusion proteins or protein fusions takes place is denoted cleavage site.

The process according to the present invention encompasses the enzymatic cleavage of fusion proteins in the junction regions by IgA protease. Within the scope of the process according to the present invention IgA protease or Igase is understood as the IgA protease of the strain Neisseria gonorrhoeae MS11 and all other enzymes which are related to this protease at the nucleotide level and with respect to their process of formation. These also include in particular the IgA proteases of the genera Neisseria and Haemophilus.

The microorganism E. coli ED 8654 was deposited at the German Collection for Microorganisms, Griesebachstraße 8, 3400 Göttingen under the number DSM 2102.

The invention is elucidated by the following examples in combination with the figures.

The figures show:

FIG. 1 shows a diagram of the protein fusion between the carrier protein MS2 polymerase (99 amino acids) and the β-domain (amino acid position 1195-1505) of the IgA protease precursor from N. gonorrhoeae MS11. The junction region between these two components consists of 12 amino acids and contains the cleavage sequence -Pro-Pro.!.-Thr-Pro- for Igase. For the construction of the cleavage site, the four oligonucleotides (1) to (4) were incorporated between the restriction cleavage sites EcoRI and HindIII. The production of the polypeptide and the cleavage with purified Igase are described in detail in Example 5.

Figure 2:
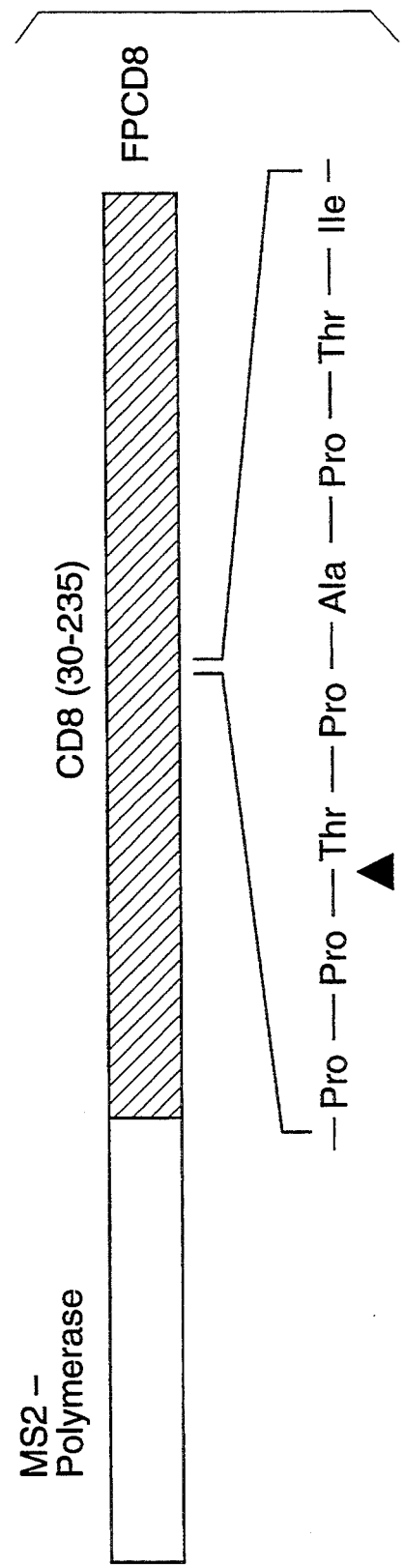

FIG. 2 shows a protein fusion consisting of the carrier protein (99 amino acids of the MS2 polymerase and 6 amino acids coded by the plasmid) and 206 amino acids of the CD8 protein from human T-lymphocytes. A natural cleavage sequence which is cleaved by Igase is located in the amino acid sequence of the CD8 protein (see Example 6).

Figure 3:
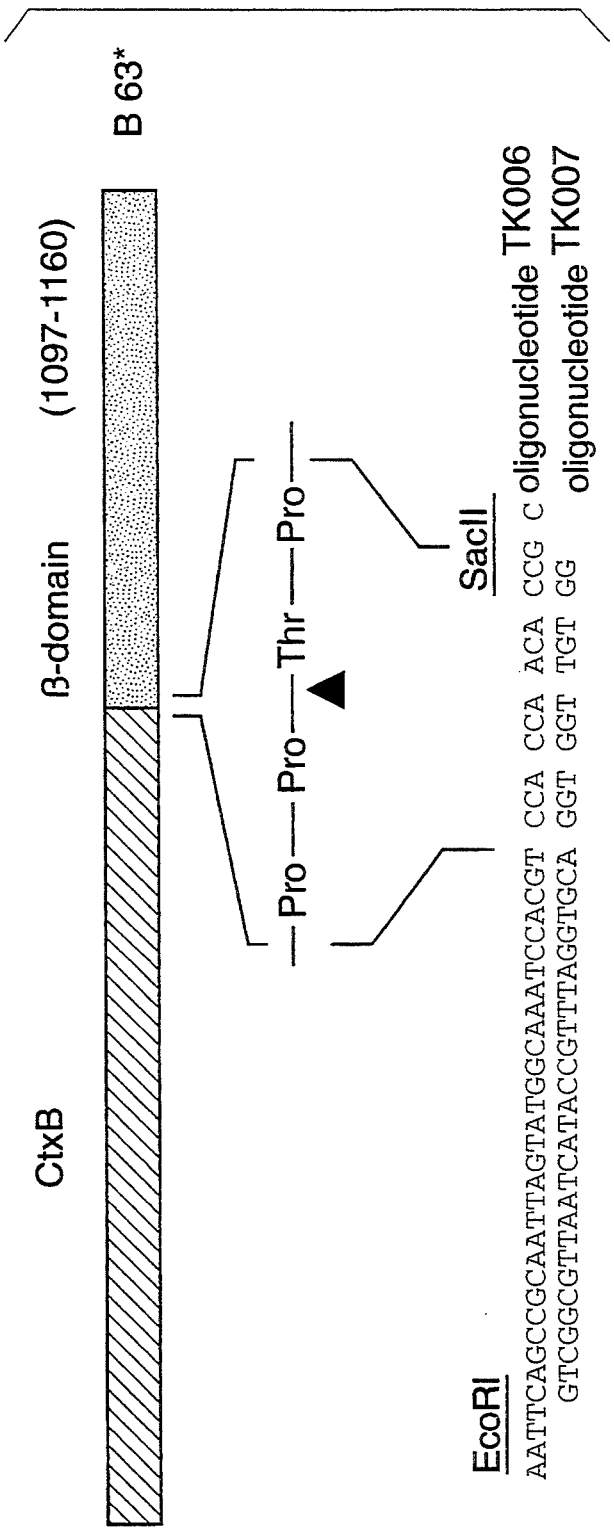

FIG. 3 shows the protein fusion B63* which was produced by E. coli cells by means of an expression secretion system. At the amino end it consists of the cholera toxin B-subunit (103 amino acids) followed by a connecting region (11 amino acids) containing the Igase cleavage site and, at the carboxyl end, a part (amino acid position 1097-1160) of the β-domain of the IgA protease precursor. The Igase cleavage site was incorporated between the two protein domains by means of the two oligonucleotides Tk006 and Tk007.

Figure 4:
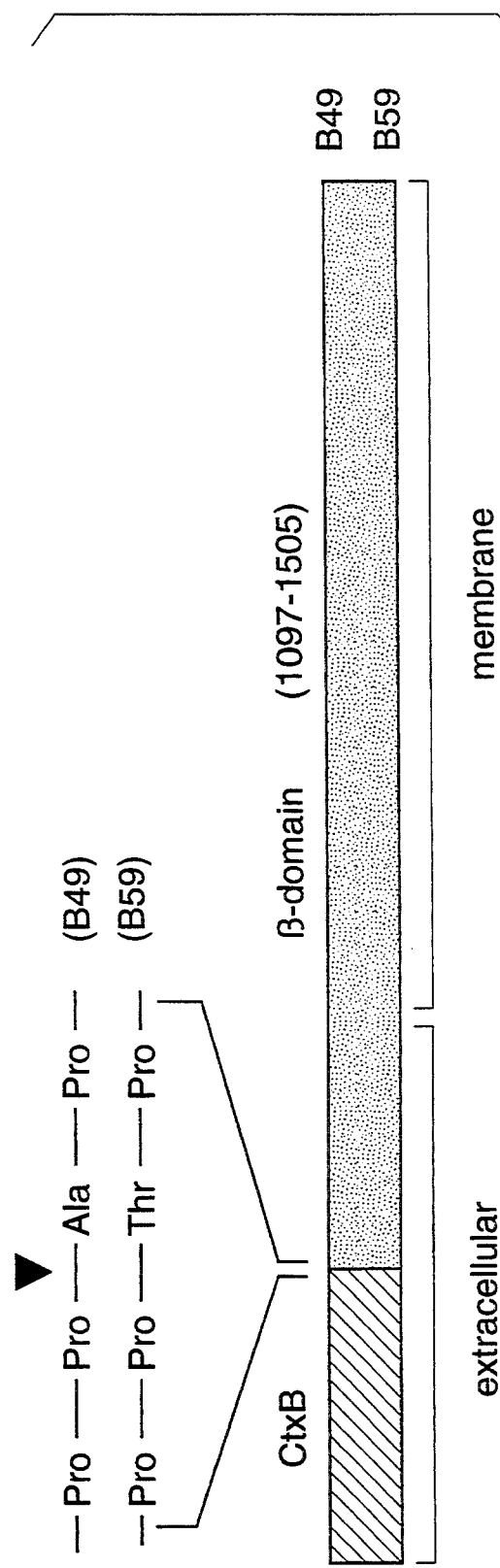

FIG. 4 shows a diagram of the protein fusions B49 and B59. They consist of the cholera toxin B-subunit and the β-domain of the IgA protease precursor. Between these components they contain two different junction regions having two different Igase cleavage sequences (-Pro-Pro-Ala-Pro- and -Pro-Pro-Thr-Pro-). The cleavage sequence was constructed with synthetic oligonucleotides (see FIG. 3).

EXAMPLE 1

Construction of a plasmid for the expression of a methionine-free G-CSF.

The construction is carried out using the expression vector pPZ07-mgllac (WO 88/09373). For this the expression vector pPZ07-mgllac is cleaved with NcoI and the protruding ends are removed with mung bean nuclease. The vector is subsequently re-cleaved with Bam HI. The IgA recognition sequence is prepared at the DNA level via the following oligonucleotides.

Oligonucleotide A:
5' AAT TCG GAG GAA AAA TTA ATG ACA CCA CTG CGA CCT CCT ACA CCA CTG GGC CCT G 3'

Oligonucleotide B:
5' GAT CC AGG GCC CAG TGG TGT AGG AGG TCG CAG TGG TGT CAT TAA TTT TTC CTC CGA ATT 3'

The two oligonucleotides are added in equimolar amounts and inserted in a ca. 100-fold excess into the vector pPZ07-mgllac which has been cleaved as described above. After religation, cells of E. coli K12 which have been made competent in the usual manner are transformed. The DNA is isolated from the cells according to conventional methods and cleaved with ApaI and Bam HI. A ca 520 bp long G-CSF fragment is isolated from the G-CSF sequence using the restriction endonucleases ApaI and Bam HI (Science 232 (1986), 61-65). This fragment is ligated into the vector which has also been cleaved with ApaI and Bam HI.

EXAMPLE 2

In addition to the IgA1 recognition sequence the fusion protein can also contain peptides which facilitate the purification. These can be composed of the DNA which encodes streptavidin. For this a streptavidin gene (WO 89/03422) is cloned in the correct translation frame before the IgA protease recognition sequence.

EXAMPLE 3

E. coli K12 cells (ED 8654, DSM 2102) are transformed with the plasmid described in Example 1, selected on the antibiotic marker (ampicillin) and the plasmid is characterized by restriction analysis. Such a clone is used for the culture and expression of G-CSF. The cells are grown in a complete medium. This medium contains per liter 16 g bactotryptone (Difco), 10 g yeast extract (Difco) and 5 g sodium chloride. The cells are allowed to grow up to an OD 546 of 2.0 and are then induced with $10^{-3}$ mol/l IPTG. After a further 4 hours the cells are harvested by centrifugation, lysed with lysozyme/EDTA and the G-CSF is isolated as inclusion bodies (IB's cf. EP-A 0 219 874).

The denaturation or renaturation of the isolated insoluble G-CSF fusion particles is carried out as described in EP-A 0 219 874. The denaturation is carried out by dialysis against 6 mol/l guanidine hydrochloride. At this point an aliquot can already be taken and after dialysis against 5 mmol/l potassium phosphate buffer, pH 7 it is used for the cleavage with IgA protease (Example 4).

As an alternative, after the denaturation with guanidine hydrochloride, a dialysis is carried out against 5 mmol/l potassium phosphate buffer pH 7 which contains 1 mmol/l GSH and 3 mmol/l GSSG. After renaturation this is also dialysed against 5 mmol/l potassium phosphate buffer, pH 7.

EXAMPLE 4

Cleavage of the fusion protein with IgA1 protease for protease for the production of a native G-CSF without methionine in position $-1$ IgA1 protease is isolated as described in EMBO Jour, 3 (1984), 1595-1601, 2-5 µg IgA protease is added to 10 µg of G-CSF which has been renatured or denatured according to Example 3 and incubated for 30 min at room temperature. The methionine-free G-CSF can be isolated over different ion-exchange columns such as Mono-Q or Mono-S. Protein sequencing of the amino-terminal end shows that the purified G-CSF begins with the correct amino acid sequence Thr(+1)-Pro(+2).

EXAMPLE 5

Production of a protein fusion and cleavage of insoluble protein aggregates from "inclusion bodies" at an Igase specific cleavage site.

The prokaryotic expression vector pEX31C (K. Strebel, Journal of Virotogy 57, 983-991, 1986) was modified in such a way that a protein fusion which was overproduced in E. coli cells using this system could be cleaved by Igase into the carrier protein and the desired protein.

For this purpose a double-stranded DNA fragment which codes for the amino acid sequence Thr-Pro-Ala-Pro-Arg -Pro-Pro.!.Thr-Pro is constructed from oligonucleotides prepared synthetically. This DNA fragment is inserted into the EcoRI cleavage site of the expression vector pEX31C using genetic engineering methods. In addition, directly adjacent to this, two further synthetic DNA fragments, which contained a series of suitable cleavage sites for restriction endonucleases and termination signals for the bacterial enzymes which participate in the gene expression, are inserted into the HindIII cleavage site. A DNA fragment which codes for the β-domain of the IgA protease precursor protein from Neisseria gonorrhoeae MS11 is inserted, using the cleavage sites for SmaI and HindIII, into the expression plasmid pEV37 which is formed in this way. By this means a hybrid gene was formed which forms a fusion protein when expressed in E. coli. This contained 99 amino acids of the MS2 polymerase at its amino end as a carrier protein, followed by a central junction region of 12 amino acids with the Igase cleavage sequence and the desired β-domain at the carboxyl end (see FIG. 1). Using purified Igase, the β-domain at the carboxyl end of the protein fusion could be cleaved off at the cleavage site Pro.!.Thr within the junction region.

The plasmid with the hybrid gene was introduced by transformation into E. coli cells which contained the regulation factor CI[857] from the bacteriophage lambda for the controllable overproduction of the protein fusion (E. Remaut, Gene 22, 103-113, 1983). The CI[857] repressor was inactivated by increasing the temperature from 28° C. to 42° C. and as a consequence the production of protein in the recombinant E. coli cells was activated. For this purpose 50 ml of an E. coli culture which had been grown for 12 h at 28° C. was transferred to 200 ml medium which had been previously pre-heated to 45° C. and cultured for a further 2 hours at 42° C. In this step the protein fusion accumulates in large amounts in the cytoplasm of the bacteria in the form of "inclusion bodies". Afterwards the bacteria were harvested by centrifugation, suspended in 20 ml lysis buffer (10% saccharose, 50 mM Tris/HCl pH 8.0, 1 mM EDTA) and, after the addition of 400 μl lysozyme solution (5 mg/ml), incubated for 30 min at 22° C. The detergent Triton X-100 was added to yield a final concentration of 0.1% and the solution was again incubated for 30 min. The DNA released by the lysis of the cells was broken up by ultrasonic treatment, the insoluble components including the protein fusion present in the precipitation bodies, was centrifuged down and subsequently washed in 5 ml U1NTE buffer (1M urea, 50 mM NaCl, 50 mM Tris/HCl pH 8.0, 1 mM EDTA). After renewed centrifugation, the sediment was suspended by sonication in 5 ml PBS buffer (20 mM potassium phosphate, pH 7.5, 140 mM NaCl) and washed. This procedure was repeated several times in order to completely remove residual urea. Finally the insoluble fraction which contained the fusion protein was suspended in 5 ml PBS buffer by sonication.

The quality and the amount of the suspended protein fusion was determined by means of SDS polyacrylamide gel electrophoresis (12.5%) and subsequent staining with Coomassie blue. For the cleavage, the protein suspension was incubated for 3 hours at 37° C. at an enzyme/substrate ratio of 1/100 (w/w). The cleavage which resulted of the non-purified and insoluble protein fusion was examined by analytical SDS polyacrylamide gel electrophoresis in which it turned out that a polypeptide had been formed which had the expected size of the β-protein. This protein was transferred onto a nitrocellulose membrane and subjected to an automated sequence analysis. The sequence of the terminal amino acids confirmed that it had been formed from the protein fusion by correct cleavage at the Igase cleavage site present.

However, in the cleavage only up to about 50% of the total amount of the substrate used was converted. No increase could be achieved by adding larger amounts of Igase and by longer reaction times. This indicates that the cleavage site for Igase is not accessible in the uncleaved portion of the fusion protein. Hybrid protein and cleavage products were still in the form of insoluble aggregates even after incubation with Igase and as a consequence were sedimented out of the suspension by centrifugation.

Cleavage yields of up to 90% were achieved if, instead of the impure "inclusion body fraction", a protein fusion was employed which had been previously subjected to an additional purification step. For this, the insoluble sediment, after being washed in U1NTE buffer (see above), was taken up in 5 ml U7NTE buffer (7M urea, 50 mM NaCl, 50 mM Tris/HCl pH 8.0, 1 mM EDTA). Insoluble components were removed by centrifugation and the soluble fraction was dialysed against 5 l PBS buffer at 4° C. During the removal of urea by dialysis, the fusion protein precipitated out of the solution in the form of insoluble aggregates. The precipitated aggregates were converted into a fine suspension by ultrasonic treatment and cleaved with Igase and analysed as described above.

EXAMPLE 6

Specific cleavage of a renatured, soluble protein fusion with Igase

By use of the pEX expression system, a hybrid protein was produced (see Example 1) which consists of the MS2 polymerase and a part of the CD8 protein of human cytotoxic T-lymphocytes (see FIG. 2). After the initial purification and solubilization of the protein from "inclusion bodies" in U7NTE buffer, a preparative 12.5% SDS polyacrylamide gel was employed as a further purification step. The protein fusion was cut out of the gel as a single band after staining with Coomassie blue and subsequently separated from the gel material according to the method of Hunkapiller (Methods in Enzymology 91, 227-235, 1983). In this process the electrolution was carried out in TAE buffer <40 mM Tris/acetate, pH 7.9) to which 0.1% SDS (sodium dodecyl sulphate) had been added. The SDS was removed later by dialysis against 5 l TAE buffer at 22° C. The protein was transferred to storage buffer (20 mM potassium phosphate, pH 7.5, 140 mM NaCl, 50% glycerol) in a further dialysis. The soluble fusion protein obtained in this way was incubated with purified Igase (see Example 5) and in this process it was completely cleaved into two polypeptide fragments at a cleavage site (-Pro -Pro-.!.Thr-Pro-Ala, see FIG. 2) contained in the CD8 molecule. The specificity of the cleavage was examined by analysis of the amino acid sequence at the amino end of the smaller cleavage product. The result of this examination was, as expected, the sequence Thr-Pro-Ala -Pro-Thr-Ile.

EXAMPLE 7

Specific cleavage by Igase of a soluble protein fusion isolated from culture supernatants A protein fusion consisting of the cholera toxin B-subunit and a part of the β-domain (Pos. 1097–1160; J. Pohlner, Nature 325, 458–462, 1987) of the Igase protease precursor from N. gonorrhoeae MS11 was isolated in soluble form from culture supernatants of recombinant E. coli cells. In order to separate the two protein components from one another an artificial cleavage sequence for Igase (Pro-Pro.!.Thr-Pro-) was inserted into the junction region between the cholera toxin B-subunit and the β-domain using genetic engineering methods. For this the oligonucleotides Tk006 and Tk007 were inserted between the restriction cleavage sites EcoRI and SacII in the junction region (see FIG. 3). The fusion protein was concentrated by precipitation with ammonium sulphate from 2 l supernatant of a bacterial culture which had been grown for 12 h at 37° C. and subsequently dialysed against 5 l PBS buffer. For the cleavage it was incubated with purified Igase for 2 h at 37° C. at a concentration of 50 μg/ml in PBS buffer at an enzyme/substrate ratio of 1/50 (w/w). An immunoblot analysis showed that the larger cleavage fragment arising from the complete cleavage corresponded to the natural cholera toxin B-subunit with regard to its molecular weight and to its reaction with antiserum.

EXAMPLE 8

Specific cleavage of protein fusions on the surface of gram-negative bacteria by means of Igase An expression-secretion system was used to outwardly expose the protein fusions TKB49 and TKB59, which consist of the cholera toxin B-subunit and the size and reaction with antiserum to the natural cholera toxin B-subunit,

EXAMPLE 9

Purification of active Igase from culture supernatants of recombinant E. coli cells Recombinant E. coli C600 cells containing the plasmid pEX1070 (DE 36 22 221.6) with a modified IgA protease gene secrete the active Igase into the culture supernatant, The enzyme could be concentrated in the culture supernatant by membrane filtration and subsequently precipitated from the solution using ammonium sulphate (0.42 g/ml). After centrifugation the sediment was dissolved in Biorex buffer (50 mM potassium phosphate, pH 7.0, 8.6% glycerol) (1 ml buffer per 1 l culture supernatant), equilibrated by dialysis against 2 l buffer and subsequently subjected to cation-exchange chromatography (Biorex 70). The bound IgA protease was eluted from the column in one step with elution buffer (500 mM potassium phosphate, pH 7.0, 8.6% glycerol) and fractionated. Fractions containing IgA protease were subsequently analysed by SDS polyacrylamide gel electrophoresis (12.5%). At this point in the purification an average degree of purity of >90% was obtained. For the preparation of the Igase in pure form, a gel filtration was carried out with Sephacryl HR300 in Biorex buffer, followed by further cation-exchange chromatography (see above). The activity of the Igase was tested by incubation with IgA1 antibodies and separation of the resulting cleavage products in an SDS polyacrylamide gel.

EXAMPLE 10

Construction of a plasmid for the expression of a methionine-free interleukin 3:

The construction is carried out using the expression vector pPZ07-mgllac (WO88/09373). For this the expression vector pPZ07-mgllac is cleaved with NCOI and the protruding ends are removed with mung bean nuclease. The vector is subsequently re-cleaved with Bam HI. The optimized amino-terminal region of the fusion protein is prepared at the DNA-level via the following oligonucleotides:

Primer 1A:

5' AATTCGGAGGAAAAATTAATGAAAGCCAAACGTTTTAAAAAACATGTCGACC
ATGGAG 3'

IgA protease β-domain, on the surface of recombinant Salmonellae, The hybrid gene coding for TKB49 contained the original cleavage sequence (c) (-Pro-Pro.!- .Ala-Pro-) for Igase in the junction region between the toxin and the β-domain, In contrast a synthetic DNA fragment consisting of the oligonucleotides Tk006 and Tk007 and which coded for the cleavage sequence (-Pro-Pro.!.Thr -Pro-) was inserted into the gene for TKB59 between the restriction cleavage sites EcoRI and SacII (see FIG. 3), When intact bacteria which carried such protein fusions anchored to their surface were incubated with purified Igase then specific cleavage at the Igase cleavage sites could be observed. Immunoblot analyses showed that the small cleavage fragments resulting from the cleavage corresponded in their Primer 1B:

5' GGATCCTCCATGGTCGACATGTTTTTTAAAACGTTTGGCTTTCATTAATTTT
TCCTCCGAATT 3'

Both oligonucleotides are added together in equimolar amounts and inserted in a ca. 100-fold excess into the vector pPZ07-mgllac which has been cleaved as described above. After ligation, cells of E. coli K12 which have been made competent in the usual manner are transformed. The DNA is isolated from the cells according to known methods, cleaved with SalI/Bam HI and ligated with a DNA fragment which contains the region coding for interleukin 3 without the signal sequence (described below).

The region coding for interleukin 3 with the recognition region for IgA protease is prepared at the DNA level by means of the well-known PCR technique in which a PCR reaction is carried out with the cDNA of interleukin 3 as the template and with the primers detailed below:

Primer 2A:

5' AAGCTTGTCGACCCACGTCCACCAGCTCCCATGACCCAGACAACGCCC 3'

Primer 2B:

5' TTCGTTGGATCCCTAAAAGATCGCGAGGCTCAAAGT 3'

The resulting PCR fragment is re-cleaved with the enzymes SalI and Bam HI and can thus be directly inserted into the vector DNA described above and covalently bound with the aid of ligase.

After transformation of the DNA in a suitable host, e.g. E. coli K12 C600, Il 3 can be synthesized in E. coli in the form of Rb's and subsequently isolated. A de- and renaturation of the protein is carried out as described for G-CSF and the renatured protein is cleaved with IgA protease. The met-free Il 3 prepared in this way can be used for therapy after further purification steps.

EXAMPLE 11

Construction of a plasmid for the expression of a methionine-free interleukin 2

The construction can be carried out using the expression vector pPZ07-mgllac (W088/09373) which has been cleaved with SalI/Bam HI after insertion of the primers 1A and 1B as described in Example 10. The region coding for interleukin 2 with the IgA protease recognition region is prepared at the DNA level by means of the PCR method, in which a PCR reaction is carried out with the cDNA of interleukin 2 as the template and the primers 3A and 3B which also code for the recognition region for the IgA protease.

Primer 3A:

5' AAGCTTGTCGACCCACGTCCACCAGCACCTACTTCAAGTTCTACAAAG 3'

Primer 3B:

5' TTCGTTGGATCCTCAAGTTAGTGTTGAGATGATGCTTT 3'

The PCR fragment obtained in this way is re-cleaved with the enzymes SalI and Bam HI and can thus be directly inserted into the vector DNA described above. The further procedure is carried out as described for Il 3. The previous example has described how methionine-free therapeutic proteins which begin with the amino acid sequence Ala Pro can be produced by suitable use of the IgA protease recognition cleavage site and the further process. Further proteins can be produced free of methionine in analogy to the previously described examples i.e. by using oligonucleotides which firstly contain the recognition region for the IgA protease as well as a region which corresponds to the 5' or the 3' end of the published sequence and can thus be prepared by means of PCR amplification. In the following further therapeutically relevant proteins are listed which begin with Ala-pro in their mature naturally occurring form and can therefore be produced in an analogous manner with the process according to the present invention:

Cathepsin L (EC 3.4.22.15), Mason, R. W. et al. Biochem. J. 240, 373–377, 1986.

Erythropoietin, Lai, P. H. et al. J. Biol. Chem. 261, 3116–3121, 1986.

Interleukin-1 beta, Zsebo, K.-M. et al. Blood 71, 962–968, 1988.

Osteonectin, Fisher, L. W. et al. J. Biol. Chem. 262, 9702–9708, 1987.

Type IV collagenase, Collier I.E. et al, J. Biol. Chem. 263, 6579–6587, 1988.

In addition, proteins can be produced in this manner which begin with the amino acid sequence Ser, Pro in their mature form. Examples of these are:

Alpha-1 antitrypsin, Hill, R. E. et al., Nature 311, 175–177, 1984.

Atrial natriuretic factor, Kambayashi, Y. et al., FEBS Lett. 259, 341–345, 1990.

Further examples of proteins which begin with Thr Pro in their mature form and which can be therapeutically relevant are for example:

Complement factor B, Campell, R. D. et al., Proc. Nat. Acad. Sci. 80, 4464–4468, 1983.

Apolipoprotein A, Eaton, D. L. et al., Proc. Nat. Acad. Sci. 84, 3224–3228, 1987.

Details of the deposit of the aforementioned microorganism are given in the following.

We claim:

1. Process for preparation of a desired component of a fusion protein, comprising:
   (a) modifying a junction region between two components of said fusion protein to form an IgA protease recognition site therein, wherein said recognition site has amino acid sequence:

Y-Pro.!.X-Pro wherein "!" is a cleavage site for said IgA protease, Y is at least one amino acid in length, and X is a single amino acid;
   (b) contacting said fusion protein with IgA protease to cleave it at !, and
   (c) isolating a desired component formed thereby.

2. Process of claim 1, comprising modifying said junction region by incorporating at least one nucleotide sequence into said junction region, said incorporating thereby forming an IgA protease recognition site in said junction region.

3. Process of claim 1, comprising modifying a junction region of a fusion protein which does not have a natural IgA protease recognition site.

4. Process of claim 1, wherein said fusion protein comprises at least one carrier component.

5. Process of claim 4, wherein said carrier component comprises at least a portion of a β galactosidase molecule.

6. Process of claim 4, wherein said carrier component comprises a plurality of charged amino acids.

7. Process of claim 4, wherein said carrier component is a peptide or protein with high affinity for a specific substance.

8. Process of claim 1, wherein X is Ser, Thr or Ala.

9. Process of claim 8, wherein X is Ser or Thr.

10. Process of claim 1, wherein Y terminates at its C terminal with a member selected from the group consisting of Pro, Pro-Ala, Arg-Pro, Pro-Arg-Pro, Ala-Pro-Arg-Pro and Pro-Ala -Pro-Arg-Pro.

11. Process of claim 1, wherein said IgA protease recognition site has an amino acid sequence selected from the group consisting of:
   a) Pro-Ala-Pro.!.Ser-Pro
   b) Pro-Pro.!.Ser-Pro
   c) Pro-Arg-Pro-Pro.!.Ala-Pro
   d) Pro-Pro.!.Thr-Pro
   e) Ala-Pro-Arg-Pro-Pro.!.Thr-Pro, and
   f) Pro-Ala-Pro-Arg-Pro-Pro.!.Thr-Pro.

12. Process for production of a desired substance, comprising:
   (a) transforming a host cell with at least one copy of a DNA sequence which codes for a fusion protein, said fusion protein having an IgA protease recognition site at a junction region between two components of said fusion protein, wherein one of said components is said desired substance, wherein said recognition site has amino acid sequence Y-Pro.!.X-Pro wherein Y is at least one amino acid, X is one amino acid, and "!" is a recognition and cleavage site for an IgA protease, (b) culturing said cell in a culture medium to express said fusion protein, (c) cleaving fusion protein expressed thereby with an IgA protease to form cleavage products, and (d) isolating said desired substance from said cleavage products.

13. Process of claim 12, wherein said DNA sequence is a vector.

14. Process of claim 12, comprising cleaving said fusion protein in said medium.

15. Process of claim 14, comprising lysing said transformed cell prior to cleaving said fusion protein.

16. Process of claim 14, comprising removing native cellular proteins prior to cleaving said fusion protein.

17. Process of claim 1, wherein said IgA protease is a Neisseria IgA protease.

18. Process of claim 1, wherein said IgA protease is a Haemophilus IgA protease.

19. Process of claim 17, wherein said Neisseria is *Neisseria gonorrhoeae* or *Neisseria meningitides*.

20. Process of claim 18, wherein said Haemophilis is *Haemophilus influenzae* or *Haemophilus aegypticus*.

21. Process of claim 1, wherein said IgA protease is a modified, natural IgA protease.

22. Process of claim 1, wherein said IgA protease is obtained from an overproducing, non-pathogenic strain of bacteria.

23. Process of claim 1, wherein said IgA protease is immobilized.

24. Process of claim 12, wherein said fusion protein is present in soluble form.

25. Process of claim 12, wherein said fusion protein is present in insoluble form.

26. Process of claim 12, wherein said fusion protein is present in membrane associated form.

27. Process of claim 12, wherein said fusion protein is present in cell bound form.

28. Process of claim 12, wherein said fusion protein is present as an inclusion body.

29. Process of claim 12, wherein said host cell is a prokaryote, said fusion protein consists of amino acid sequence Met-Y-Pro-↓-X-Pro-A wherein X is one amino acid, Y is at least one amino acid, and A is at least one amino acid.

30. Process of claim 29, wherein said desired substance has amino acid beginning with sequence X-Pro.

31. Process of claim 29, wherein X-Pro-A is human granulocyte colony stimulating factor or a derivative thereof.

32. Process of claim 29, further comprising treating cleavage product X-Pro-A with a dipeptidyl aminopeptidase to cleave x-Pro therefrom.

33. Fusion protein comprising a plurality of polypeptide components, said fusion protein having at least one IgA protease recognition site, said recognition site having amino acid sequence:

Y-Pro-↓-X-Pro wherein X is any amino acid and Y is one or more amino acid, wherein each said recognition site is positioned in a junction region between two polypeptide components of said fusion protein.

34. The fusion protein of claim 33, wherein said fusion protein consists of amino acid sequence Y-Pro-↓-X-Pro-A, wherein A is at least one amino acid long.

35. The fusion protein of claim 33, wherein X is an amino acid selected from the group consisting of Ser, Thr, and Ala.

36. The fusion protein of claim 33, wherein Y has a C terminus selected from the group consisting of Pro, Pro-Ala, Pro-Arg-Pro, Ala-Pro-Arg-Pro, and Pro-Ala-Pro-Arg-Pro.

37. The fusion protein of claim 34, wherein x-Pro-A is human granulocyte colony stimulating factor or a derivative thereof.

38. Recombinant prokaryotically produced mature granulocyte colony stimulating factor (G-CSF), wherein said G-CSF has an N-terminal sequence Thr-Pro.

39. Composition comprising the G-CSF of claim 38 and less than 0.1% of other proteins.

40. The composition of claim 39, having less than $10^{-3}$% of other proteins.

41. The composition of claim 39, further comprising a member selected from the group consisting of a pharmaceutical additive, an auxiliary agent, and a pharmaceutical carrier.

42. Isolated nucleic acid sequence coding for the fusion protein of claim 33.

43. Isolated nucleic acid sequence coding for the fusion protein of claim 34.

44. Isolated nucleic acid sequence coding for the fusion protein of claim 35.

45. Recombinant vector comprising the isolated nucleic acid sequence of claim 44, operably linked to a promoter.

46. Recombinant vector comprising the isolated nucleic acid sequence of claim 43 operably linked to a promoter.

47. The recombinant vector of claim 45, wherein said promoter is inducible.

48. The recombinant vector of claim 46, wherein said promoter is inducible.

49. The recombinant vector of claim 46, wherein said vector is a prokaryotic vector.

50. The recombinant vector of claim 45, wherein said vector is a prokaryotic vector.

51. The recombinant vector of claim 47, wherein said vector is a prokaryotic vector.

52. The recombinant vector of claim 48, wherein said vector is a prokaryotic vector.

53. The recombinant vector of claim 45, wherein said vector is a plasmid.

54. The recombinant vector of claim 46, wherein said vector is a plasmid.

55. Cell transformed with the nucleic acid sequence of claim 42.

56. The cell of claim 55, wherein said cell is a prokaryote.

57. Recombinant prokaryotically produced mature G-CSF having an N-terminal sequence Thr-Pro produced by the process of;

(a) expressing a fusion protein forming an IgA protease recognition site between a first and second region, wherein said second region encodes mature G-CSF having an N-terminal sequence Thr-Pro and said recognition site has an amino acid sequence:

Y-Pro-!-Thr-Pro wherein "!" is a cleavage site for said IgA protease and Y is at least one amino acid in length, (b) contacting said fusion protein with an IgA protease to cleave it at !, and
(c) isolating mature G-CSF having an N-terminal sequence Thr-Pro.

* * * * *

SEQUENCE LISTING ( 1 ) GENERAL INFORMATION:

( i i i ) NUMBER OF SEQUENCES: 21

( 2 ) INFORMATION FOR SEQ ID NO: 1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 1:

Ile  Gly  Gly  Arg  Xaa
                         5

(2) INFORMATION FOR SEQ ID NO: 2:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 2:

Pro Ala Pro Ser Pro
                 5

(2) INFORMATION FOR SEQ ID NO: 3:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 3:

Pro Pro Ser Pro (2) INFORMATION FOR SEQ ID NO: 4:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 4:

Pro Pro Ala Pro (2) INFORMATION FOR SEQ ID NO: 5:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 5:

Pro Pro Thr Pro (2) INFORMATION FOR SEQ ID NO: 6:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 6:

Ala Pro Arg Pro (2) INFORMATION FOR SEQ ID NO: 7:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 7:

Pro Ala Pro Arg Pro
5

( 2 ) INFORMATION FOR SEQ ID NO: 8:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 8:

Pro Arg Pro Pro Ala Pro
5

( 2 ) INFORMATION FOR SEQ ID NO: 9:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 9:

Ala Pro Arg Pro Pro Thr Pro
5

( 2 ) INFORMATION FOR SEQ ID NO: 10:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 10:

Pro Ala Pro Arg Pro Pro Thr Pro
5

( 2 ) INFORMATION FOR SEQ ID NO: 11:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 11:

Met Xaa Pro Xaa Pro Xaa
5

( 2 ) INFORMATION FOR SEQ ID NO: 12:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 12:

Pro Arg Pro Pro ( 2 ) INFORMATION FOR SEQ ID NO: 13:

( i ) SEQUENCE CHARACTERISTICS:
        ( A ) LENGTH: 5 amino acids (B) TYPE: amino acid
(D) TOPOLOGY: linear (ii) MOLECULE TYPE: protein (xi) SEQUENCE DESCRIPTION: SEQ ID NO: 13:

Ala Pro Arg Pro Pro
                 5

(2) INFORMATION FOR SEQ ID NO: 14:

(i) SEQUENCE CHARACTERISTICS:
    (A) LENGTH: 6 amino acids
    (B) TYPE: amino acid
    (D) TOPOLOGY: linear (ii) MOLECULE TYPE: amino acid (xi) SEQUENCE DESCRIPTION: SEQ ID NO: 14:

Pro Ala Pro Arg Pro Pro
                     5

(2) INFORMATION FOR SEQ ID NO: 15:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (xi) SEQUENCE DESCRIPTION: SEQ ID NO: 15:

AATTCGGAGG AAAAATTAAT GACACCACTG CGACCTCCTA CACCACTGGG    50

CCTG    54

(2) INFORMATION FOR SEQ ID NO: 16:

(i) SEQUENCE CHARACTERISTICS:
    (A) LENGTH: 59 base pairs
    (B) TYPE: nucleotide
    (C) STRANDEDNESS: single
    (D) TOPOLOGY: linear (xi) SEQUENCE DESCRIPTION: SEQ ID NO: 16:

GATCCAGGGC CCAGTGGTGT AGGAGGTCGC AGTGGTGTCA TTAATTTTTC    50

CTCCGAATT    59

(2) INFORMATION FOR SEQ ID NO: 17:

(i) SEQUENCE CHARACTERISTICS:
    (A) LENGTH: 63 base pairs
    (B) TYPE: nucleic acid
    (C) STRANDEDNESS: single
    (D) TOPOLOGY: linear (xi) SEQUENCE DESCRIPTION: SEQ ID NO: 17:

GGATCCTCCA TGGTCGACAT GTTTTTTAAA ACGTTTGGCT TTCATTAATT    50

TTTCCTCCGA ATT    63

(2) INFORMATION FOR SEQ ID NO: 18:

(i) SEQUENCE CHARACTERISTICS:
    (A) LENGTH: 48 base pairs
    (B) TYPE: nucleic acid
    (C) STRANDEDNESS: single
    (D) TOPOLOGY: linear (xi) SEQUENCE DESCRIPTION: SEQ ID NO: 18:

AAGCTTGTCG ACCCACGTCC ACCAGCTCCC ATGACCCAGA CAACGCCC    48

( 2 ) INFORMATION FOR SEQ ID NO: 19:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO: 19:

TTCGTTGGAT CCCTAAAAGA TCGGCAGGCT CAAAGT                36

( 2 ) INFORMATION FOR SEQ ID NO: 20:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( x i ) SEQUENCE DESCRIPTION: SEQ ID NO: 20:

AAGCTTGTCG ACCCACGTCC ACCAGCACCT ACTTCAAGTT CTACAAAG    48

( 2 ) INFORMATION FOR SEQ ID NO: 21:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO: 21:

TTCGTTGGAT CCTCAAGTTA GTGTTGAGAT GATGCTTT              38